United States Patent
Mukhopadhyay et al.

(10) Patent No.: US 11,039,792 B2
(45) Date of Patent: Jun. 22, 2021

(54) SYSTEM AND METHOD FOR HEART RATE ESTIMATION

(71) Applicant: Tata Consultancy Services Limited, Mumbai (IN)

(72) Inventors: Shalini Mukhopadhyay, Kolkata (IN); Nasimuddin Ahmed, Kolkata (IN); Avik Ghose, Kolkata (IN); Arijit Sinharay, Kolkata (IN); Dibyanshu Jaiswal, Kolkata (IN); Arijit Chowdhury, Kolkata (IN); Ramu Reddy Vempada, Kolkata (IN); Tapas Chakravarty, Kolkata (IN); Arpan Pal, Kolkata (IN)

(73) Assignee: TATA CONSULTANCY SERVICES LIMITED, Mumbai (IN)

(*) Notice: Subject to any disclaimer, the term of this patent is extended or adjusted under 35 U.S.C. 154(b) by 516 days.

(21) Appl. No.: 15/869,207

(22) Filed: Jan. 12, 2018

(65) Prior Publication Data
US 2018/0338727 A1    Nov. 29, 2018

(30) Foreign Application Priority Data
May 25, 2017  (IN) ............................. 201721018447

(51) Int. Cl.
A61B 5/024    (2006.01)
A61B 5/00     (2006.01)
G16H 40/63    (2018.01)

(52) U.S. Cl.
CPC .......... *A61B 5/721* (2013.01); *A61B 5/02416* (2013.01); *A61B 5/02438* (2013.01);
(Continued)

(58) Field of Classification Search
CPC ... A61B 5/721; A61B 5/02416; A61B 5/7203; A61B 5/7267; A61B 2562/0219
See application file for complete search history.

(56) References Cited

U.S. PATENT DOCUMENTS

| 4,911,167 | A  | * | 3/1990 | Corenman | A61B 5/0245 600/324 |
| 7,003,751 | B1 | * | 2/2006 | Stroomer | G06F 30/30 716/102 |

(Continued)

FOREIGN PATENT DOCUMENTS

WO    WO-2009/063463    5/2009

OTHER PUBLICATIONS

Barde, M. P., & Barde, P. J. (2012). What to use to express the variability of data: Standard deviation or standard error of mean?. Perspectives in clinical research, 3(3), 113. (Year: 2012).*

(Continued)

*Primary Examiner* — Tse W Chen
*Assistant Examiner* — Connor William Blake
(74) *Attorney, Agent, or Firm* — Finnegan, Henderson, Farabow, Garrett & Dunner LLP

(57) ABSTRACT

Techniques for heart rate estimation are disclosed. In an embodiment, synchronized photoplethysmograph (PPG) and 3-axis acceleration signals are received. Further, the PPG and acceleration signals are partitioned into windows. Furthermore, it is determined whether motion is present in a window of the acceleration signal. Moreover, Fourier transform is performed on the signals to obtain power spectra of the signals in the window when there is motion. Also, it is determined whether a peak of the acceleration signal is present in a range around first highest PPG peak. Further, it is determined whether the peak of the acceleration signal affects heart rate of the user when the peak of the acceleration signal is in the range around the highest PPG peak. The heart rate of the user in the window is then estimated using second highest PPG peak when the peak of the acceleration signal affects heart rate of the user.

13 Claims, 4 Drawing Sheets

(52) U.S. Cl.
CPC ............ *A61B 5/7203* (2013.01); *A61B 5/725* (2013.01); *A61B 5/7239* (2013.01); *A61B 5/7246* (2013.01); *A61B 5/7257* (2013.01); *A61B 5/7267* (2013.01); *A61B 2503/22* (2013.01); *A61B 2562/0219* (2013.01); *G16H 40/63* (2018.01)

(56) References Cited

U.S. PATENT DOCUMENTS

| | | | | |
|---|---|---|---|---|
| 7,680,531 | B2* | 3/2010 | Graupe | A61B 5/4362 600/511 |
| 8,437,824 | B2* | 5/2013 | Moon | A61B 5/746 600/336 |
| 9,339,236 | B2* | 5/2016 | Frix | A61B 5/1121 |
| 2004/0034294 | A1* | 2/2004 | Kimball | A61B 5/14552 600/323 |
| 2007/0004977 | A1* | 1/2007 | Norris | A61B 5/7203 600/336 |
| 2011/0066007 | A1* | 3/2011 | Banet | A61B 5/1116 600/301 |
| 2011/0224518 | A1* | 9/2011 | Tindi | A61B 5/14552 600/323 |
| 2011/0230744 | A1* | 9/2011 | Ribas Ripoll | A61B 5/1455 600/365 |
| 2012/0179011 | A1* | 7/2012 | Moon | A61B 5/14551 600/324 |
| 2013/0072775 | A1* | 3/2013 | Rogers | A61B 5/4836 600/378 |
| 2014/0073486 | A1* | 3/2014 | Ahmed | A61B 5/02438 482/9 |
| 2014/0275852 | A1* | 9/2014 | Hong | A61B 5/0205 600/301 |
| 2015/0190077 | A1* | 7/2015 | Kim | A61B 5/14551 600/301 |
| 2015/0265217 | A1* | 9/2015 | Penders | A61B 5/721 600/301 |
| 2015/0302158 | A1* | 10/2015 | Morris | G06K 9/00563 702/19 |
| 2016/0007934 | A1* | 1/2016 | Arnold | A61B 5/681 600/595 |
| 2016/0094899 | A1* | 3/2016 | Aumer | A61B 5/6802 340/870.07 |
| 2016/0256114 | A1* | 9/2016 | Chen | A61B 5/7267 |
| 2016/0324477 | A1* | 11/2016 | Gunturi | A61B 5/721 |
| 2017/0258405 | A1* | 9/2017 | Sato | A61B 5/7257 |
| 2018/0279958 | A1* | 10/2018 | Pamula | A61B 5/11 |
| 2019/0192079 | A1* | 6/2019 | Groenendaal | A61B 5/7253 |

OTHER PUBLICATIONS

Ye, Y., He, W., Cheng, Y., Huang, W., & Zhang, Z. (Feb. 16, 2017). A robust random forest-based approach for heart rate monitoring using photoplethysmography signal contaminated by intense motion artifacts. Sensors, 17(2), 385. (Year: 2017).*

* cited by examiner

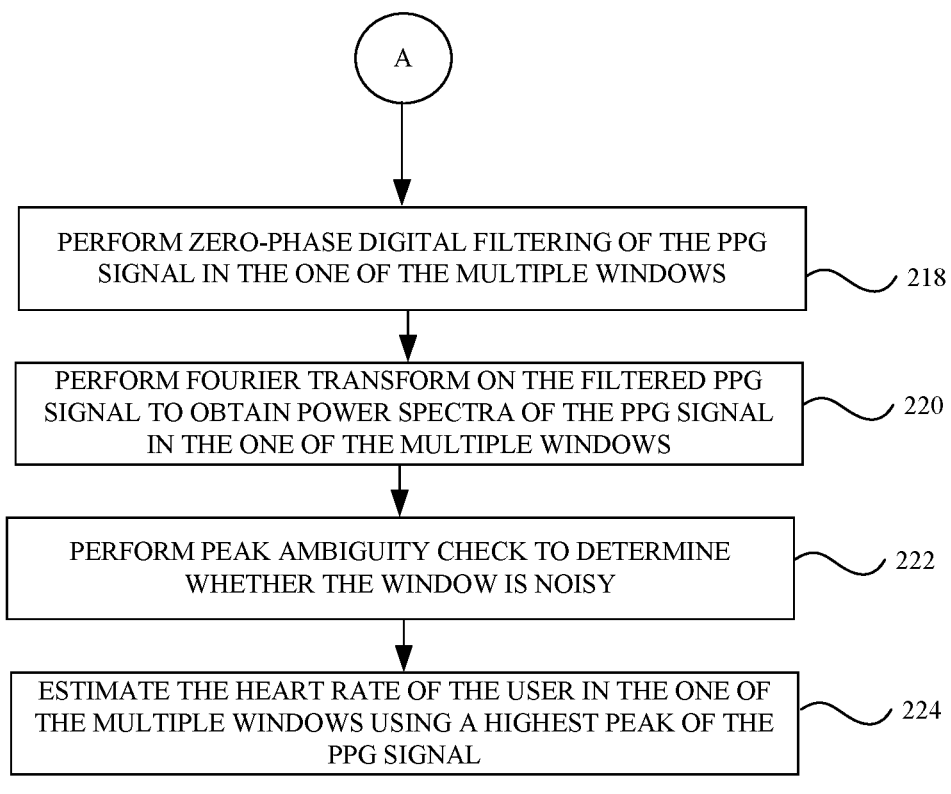
FIG. 2B    200B

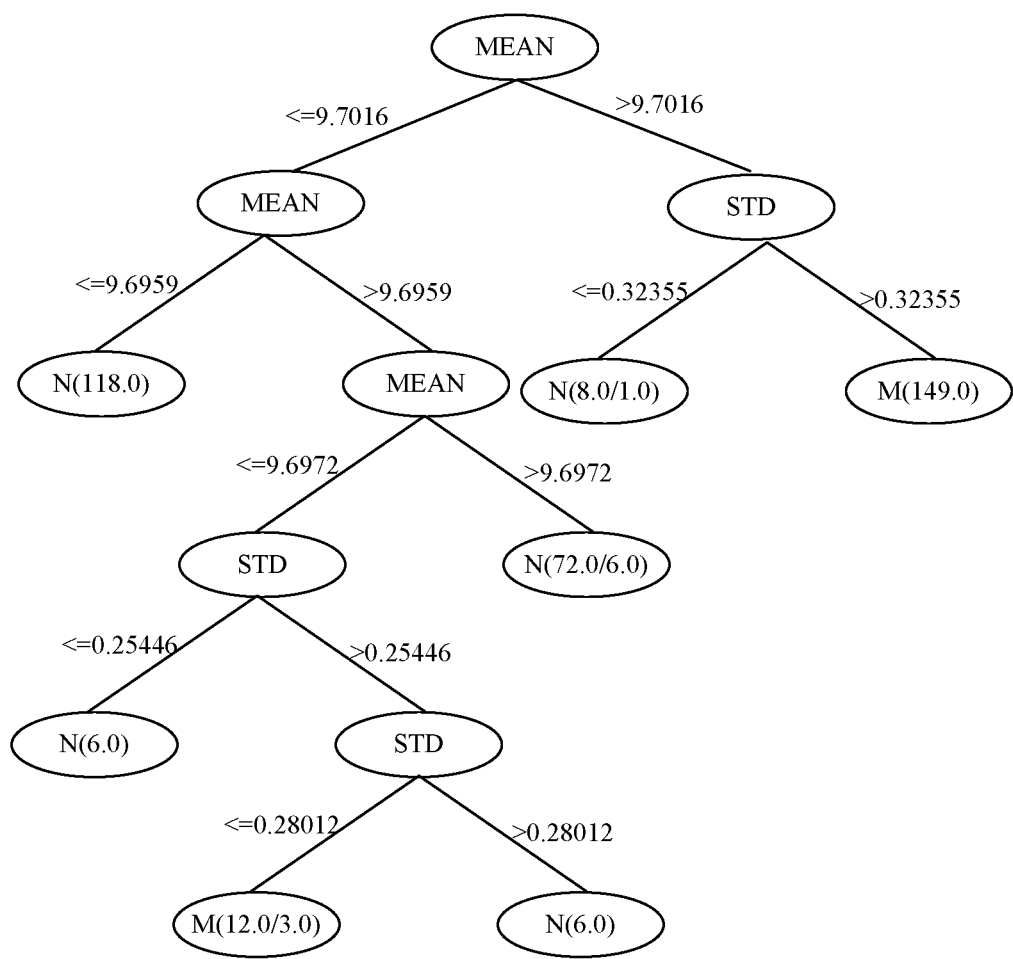
FIG. 3                300

SYSTEM AND METHOD FOR HEART RATE ESTIMATION

PRIORITY CLAIM

This U.S. patent application claims priority under 35 U.S.C. § 119 to: India Application No. 201721018447, filed on May 25, 2017. The entire contents of the aforementioned application are incorporated herein by reference.

TECHNICAL FIELD

This disclosure relates generally to heart rate estimation, and more particularly to system and method for heart rate estimation using synchronized photoplethysmograph (PPG) and 3-axis acceleration signals.

BACKGROUND

Now-a-days, heart rate estimation methods using wearable devices is of high importance, especially in crane workers or steel plants where the environment is very hazardous and requires continuous health monitoring. Generally, estimation of heart rate from a photoplethysmograph (PPG) signal obtained through a wearable device is prone to errors due to the effects of motion on the PPG signal. Also, the accuracy in measurement is affected by crane vibrations and hand movements of the workers which introduce noise and distort the PPG signal. Existing heart rate estimation techniques may require more resources and are not very feasible on low-cost real-time wearable devices. Also, the existing techniques involve high levels of computation and hence large memory space and complicated hardware may be required.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides methods and systems for heart rate estimation. In one aspect, a processor-implemented method includes steps of: (a) receiving synchronized photoplethysmograph (PPG) signal and 3-axis acceleration signal from sensors associated with the user; (b) partitioning the received PPG signal and 3-axis acceleration signal into multiple windows; (c) determining whether motion is present in one of the multiple windows of the 3-axis acceleration signal based on mean and standard deviation values of the 3-axis acceleration signal in the one of the multiple windows; (d) performing Fourier transform on the 3-axis acceleration signal and PPG signal to obtain power spectra of the 3-axis acceleration signal and PPG signal in the one of the multiple windows when there is motion in the one of the multiple windows of the 3-axis acceleration signal, wherein the power spectra comprises fast Fourier transform (FFT) peaks of the 3-axis acceleration signal and PPG signal in the one of the multiple windows; (e) determining whether a peak of the 3-axis acceleration signal is present in a range around a first highest peak of the PPG signal; (f) determining whether the peak of the 3-axis acceleration signal affects heart rate of the user by performing random forest learning when the peak of the 3-axis acceleration signal is in the range around the first highest peak of the PPG signal; and (g) estimating the heart rate of the user in the one of the multiple windows using a second highest peak of the PPG signal when the peak of the 3-axis acceleration signal affects heart rate of the user.

In another aspect, a system for heart rate estimation is provided. The system includes one or more memories; and one or more hardware processors, the one or more memories coupled to the one or more hardware processors wherein the one or more hardware processors are capable of executing programmed instructions stored in the one or more memories to: (a) receive a synchronized photoplethysmograph (PPG) signal and 3-axis acceleration signal from the multiple sensors associated with the user; (b) partition the received PPG signal and 3-axis acceleration signal into multiple windows; (c) determine whether motion is present in one of the multiple windows of the 3-axis acceleration signal based on mean and standard deviation values of the 3-axis acceleration signal in the one of the multiple windows; (d) perform Fourier transform on the 3-axis acceleration signal and PPG signal to obtain power spectra of the 3-axis acceleration signal and PPG signal in the one of the multiple windows when there is motion in the one of the multiple windows of the 3-axis acceleration signal, wherein the power spectra comprises fast Fourier transform (FFT) peaks of the 3-axis acceleration signal and PPG signal in the one of the multiple windows; (e) determine whether a peak of the 3-axis acceleration signal is present in a range around a first highest peak of the PPG signal; (f) determine whether the peak of the 3-axis acceleration signal affects heart rate of the user by performing random forest learning when the peak of the 3-axis acceleration signal is in the range around the first highest peak of the PPG signal; and (g) estimate the heart rate of the user in the one of the multiple windows using a second highest peak of the PPG signal when the peak of the 3-axis acceleration signal affects heart rate of the user.

In yet another aspect, a non-transitory computer-readable medium having embodied thereon a computer program for executing a method for heart rate estimation. The method includes steps of: (a) receiving a synchronized photoplethysmograph (PPG) signal and 3-axis acceleration signal from sensors associated with the user; (b) partitioning the received PPG signal and 3-axis acceleration signal into multiple windows; (c) determining whether motion is present in one of the multiple windows of the 3-axis acceleration signal based on mean and standard deviation values of the 3-axis acceleration signal in the one of the multiple windows; (d) performing Fourier transform on the 3-axis acceleration signal and PPG signal to obtain power spectra of the 3-axis acceleration signal and PPG signal in the one of the multiple windows when there is motion in the one of the multiple windows of the 3-axis acceleration signal, wherein the power spectra comprises fast Fourier transform (FFT) peaks of the 3-axis acceleration signal and PPG signal in the one of the multiple windows; (e) determining whether a peak of the 3-axis acceleration signal is present in a range around a first highest peak of the PPG signal; (f) determining whether the peak of the 3-axis acceleration signal affects heart rate of the user by performing random forest learning when the peak of the 3-axis acceleration signal is in the range around the first highest peak of the PPG signal; and (g) estimating the heart rate of the user in the one of the multiple windows using a second highest peak of the PPG signal when the peak of the 3-axis acceleration signal affects heart rate of the user.

It should be appreciated by those skilled in the art that any block diagram herein represents conceptual views of illustrative systems embodying the principles of the present subject matter. Similarly, it is appreciated that any flow charts, flow diagrams, state transition diagrams, pseudo code, and the like represent various processes which may be substantially represented in computer readable medium and so executed by a computing device or processor, whether or not such computing device or processor is explicitly shown.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and modules.

FIGS. 2A and 2B illustrate flow diagrams of a method for heart rate estimation, in accordance with an example embodiment.

FIG. 3 illustrates a decision tree, in accordance with an example embodiment.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The present subject matter herein provides a system and method for heart rate estimation using wearable devices, in accordance with an example embodiment. The present subject matter proposes a technique that eliminates motion artifacts while estimating heart rate from photoplethysmograph (PPG) signals. It first takes two signals i.e., PPG and 3-axis acceleration from a wearable device at a particular point of time. The PPG signal is pre-processed and the acceleration signals are tested for mobility. For example, mobility test is done using a threshold calculated by standard deviation and decision tree. Further, power spectra of the signals are obtained by Fourier transform (FFT). The initial heart rate value is estimated from a highest peak of PPG Spectrum. Then the acceleration spectra are checked for any significant peak near the assumed heart peak. The decision, whether the acceleration peak is significant is taken using two peak features in random forest learning. If no such acceleration peak is found, the heart rate is estimated and is sent for post processing. Otherwise, the second highest PPG peak is obtained and the heart rate is estimated from this peak and it is sent for post processing. In post processing, the heart rates obtained from windows are taken in a server and a final heart rate is estimated with the help of histogram where a median value of most frequently occurring bin is selected as final heart rate.

The methods and systems are not limited to the specific embodiments described herein. In addition, the method and system can be practiced independently and separately from other modules and methods described herein. Each device element/module and method can be used in combination with other elements/modules and other methods.

Figure 1:
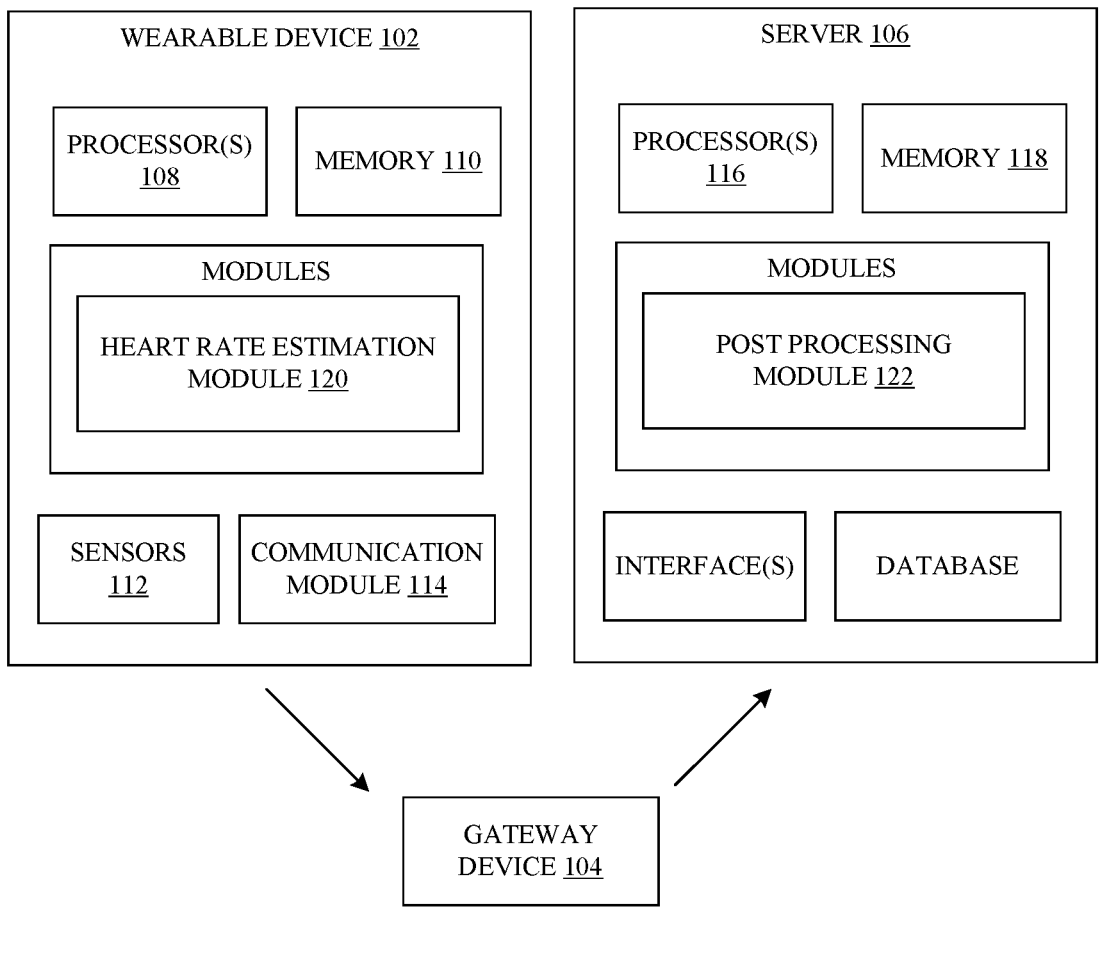
FIG. 1 illustrates a block diagram of a system for heart rate estimation, in accordance with an example embodiment.

The manner, in which the system and method for heart rate estimation, has been explained in details with respect to the FIGS. 1 through 3. While aspects of described methods and systems for heart rate estimation can be implemented in any number of different systems, utility environments, and/or configurations, the embodiments are described in the context of the following exemplary system(s).

FIG. 1 illustrates a block diagram of a system 100 for heart rate estimation, in accordance with an example embodiment. In an example embodiment, the system 100 includes a wearable device 102, a gateway device 104 and a server 106. For example, the wearable device 102 and server 106 are communicatively coupled to each other via the gateway device 104. As shown in FIG. 1, the wearable device 102 includes or is otherwise in communication with one or more hardware processors such as processor(s) 108, one or more memories such as a memory 110, sensors 112 (i.e., a PPG sensor and 3-axis acceleration sensor) and a communication module 114. In an embodiment, the processor 108, memory 110, sensors 112 and communication module 114 (e.g., Bluetooth and the like) may be coupled by a system bus such as a system bus or a similar mechanism. The wearable device 102 is communicatively coupled to the gateway device 104 via the communication module 114. Further, the server 106 includes or is otherwise in communication with one or more hardware processors such as processor(s) 116 and one or more memories such as a memory 118. Although FIG. 1 shows example components of the system 100, in other implementations, the system 100 may contain fewer components, additional components, different components, or differently arranged components than depicted in FIG. 1.

The processor 108 or 116 may include circuitry implementing, among others, audio and logic functions associated with the communication. For example, the processor 108 or 116 may include, but are not limited to, microcontroller, one or more digital signal processors (DSPs), one or more microprocessor, one or more special-purpose computer chips, one or more field-programmable gate arrays (FPGAs), one or more application-specific integrated circuits (ASICs), one or more computer(s), various analog to digital converters, digital to analog converters, and/or other support circuits. The processor 108 or 116 thus may also include the functionality to encode messages and/or data or information. The processor 108 or 116 may include, among other things, a clock, an arithmetic logic unit (ALU) and logic gates configured to support operation of the processor 108. Further, the processor 108 or 116 may include functionality to execute one or more software programs, which may be stored in the memory 110 or 118, respectively, or otherwise accessible to the processor 108 or 116, respectively.

The functions of the various elements shown in the figure, including any functional blocks labeled as "processor(s)", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" should not be construed to refer exclusively to hardware capable of executing software, and may implicitly include, without limitation DSP hardware, network processor, application specific integrated circuit (ASIC), FPGA, read only memory (ROM) for storing software, random access memory (RAM), and non-volatile storage. Other hardware, conventional, and/or custom, may also be included.

The one or more memories such as the memory 110 or 118, may store any number of pieces of information, and data, used by the system to implement the functions of the system. The memory 110 or 118 may include for example, volatile memory and/or non-volatile memory. Examples of volatile memory may include, but are not limited to volatile random access memory. The non-volatile memory may additionally or alternatively comprise an electrically erasable programmable read only memory (EEPROM), flash memory, hard drive, or the like. Some examples of the volatile memory includes, but are not limited to, random access memory, dynamic random access memory, static random access memory, and the like. Some example of the non-volatile memory includes, but are not limited to, hard disks, magnetic tapes, optical disks, programmable read only memory, erasable programmable read only memory, electrically erasable programmable read only memory, flash memory, and the like. The memory 110 or 118 may be configured to store information, data, applications, instructions or the like for enabling the wearable device 102 or 106, respectively, to carry out various functions in accordance with various example embodiments. Additionally or alternatively, the memory 110 or 118 may be configured to store instructions which when executed by the processor 108 or 116 causes the wearable device 102 or server 106, respectively, to behave in a manner as described in various embodiments. The memory 110 includes a heart rate estimation module 120 and other modules. The module 120 and other modules include routines, programs, objects, components, data structures, etc., which perform particular tasks or implement particular abstract data types. The other modules may include programs or coded instructions that supplement applications and functions of the wearable device 102. The memory 118 includes a post processing module 122 and other modules. The module 122 and other modules include routines, programs, objects, components, data structures, etc., which perform particular tasks or implement particular abstract data types. The other modules may include programs or coded instructions that supplement applications and functions of the server 106.

In operation, the sensors 112 receive input signals (i.e., a PPG signal and a 3-axis acceleration signal obtained at same point of time) from user wearing the device 102, processed for heart-rate estimation with the help of the processor 108 and memory 110, and the calculated heart rate value for each window is sent to the gateway device 104 through the communication module (Bluetooth) 114. Since data streaming is very energy consuming, Bluetooth is used to transfer the calculated heart rate values to the server 106, instead of streaming the raw PPG and acceleration data. The gateway device 104 sends the data through a network to the server 106 where the post processing part takes place.

In an example implementation, the sensors receive input signals from the user wearing the device 102. The raw PPG and 3-axis acceleration signals obtained from the wearable device are the input signals. The PPG and the 3 accelerometer signals must be in synchronization and have a fixed sampling rate (say, Fs). Further, the heart rate estimation module 120 obtains the signals and divides the signals into a plurality of windows. In an embodiment, the heart rate estimation module 120 divides the signals of PPG and 3-axis acceleration into smaller windows (of a certain fixed duration) for further processing and analysis.

Furthermore, the heart rate estimation module 120 preprocess the signals. During pre-processing, the heart rate estimation module 120 performs PPG signal threshold checking for signal quality validation and involves zero-phase filtering to extract the actual shape. In an example, this checking is to ensure that the wearable device 102 (in this case, a watch) is worn on the wrist with the help of a threshold value for the raw signal, and hence noise signals are eliminated. Further during pre-processing, the heart rate estimation module 120 subtracts the signal mean to remove direct current (DC) component from the signal.

In addition, the heart rate estimation module 120 performs mobility checking in one of the windows of the 3-axis acceleration signal. This checking is primarily done to find whether there is motion during this window. The heart rate estimation module 120 performs mobility checking with the help of a threshold value of the raw signals calculated using standard deviation of the raw time-signal amplitude and then applying a decision tree. In an example implementation, the heart rate estimation module 120 performs a modest yet a robust algorithm incorporating statistical features and decision tree base technique to determine the motion in a particular time window of the 3-axis acceleration signal. Generally, decision trees are powerful and popular tools for classification and prediction. The decision trees cater different rules, constructed in top down manner to realize the prediction and can be implemented easily, various if else conditions are employed according to the nodes of decision tree.

In an embodiment, while in motion the resultant value of the 3 axis accelerometer signal increases significantly compare to the static mode. This variation is captured in the form of mean and standard deviation of a time window of the resultant accelerometer. The time window is defined as 10 seconds. The heart rate estimation module 120 calculates the resultant value by the following equation:

$$ResVal=\sqrt{(x^2+y^2+z^2)};$$

Further, for each time window, the heart rate estimation module 120 gathers a number of resultant values and calculates mean and standard deviation (STD) of those resultant values accordingly. Furthermore, the heart rate estimation module 120 enables off line training and deploys a model decision tree to determine the mobility. In training mode, the ground truth observation is captured through the user intervention. To simulate an environment (e.g., a crane environment), the test subject is instructed to perform some specific movement for the stipulated time, incidentally the user emulates the actual crane operator and performs the experiment. The observer governs the whole procedure, meanwhile provides the instruction and annotates the events as static or motion accordingly. For every time window, the mean and standard deviation of resultant values of 3 axis accelerometer signal are denoted as features and mobility flag represents the class. One typical representations of the particular training window is as follows:

mean_window1,std_window1:S
mean_window2,std_window2:M where S denotes a static mode, M represents motion and mean_window, std_window represents the mean and standard deviation, respectively.

In addition, the heart rate estimation module 120 feed numerous such windows for the training which generates a decision tree (if else ladder) for reliable estimation of the motion for a window. An example decision tree rule 300 is shown in FIG. 3. The decision tree is implemented in the wearable device 102 as if-else ladder. In testing phase, the mean and standard deviation is calculated and implied to the decision tree for the decision of mobility. If there is motion present, the heart rate estimation module 120 performs motion removal algorithm, otherwise, peak threshold checking (to discard windows with ambiguous PPG peaks) is done and the heart rate is estimated for this window directly by fast Fourier transform (FFT) method. Thus saving power and processing inside the wearable device 102.

Moreover, if motion is present, the heart rate estimation module 120 performs PPG and acceleration signal filtering using Filtfilt. The filter 'filtfilt' performs zero-phase digital filtering by processing the input data in both the forward and reverse directions. After filtering the data in the forward direction, filtfilt reverses the filtered sequence and runs it back through the filter. The result has the following characteristics-zero-phase distortion, a filter transfer function, which equals the squared magnitude of the original filter transfer function and a filter order that is double the order of the filter specified by numerator and denominator coefficients. This is applicable in heart rate estimation module where FFT peaks are necessary and phase information is not required. The heart rate estimation module 120 filters the pre-processed signal with a lower cut-off frequency of 0.75 Hz (heart rate 45 BPM) and a higher cut-off frequency of 3 Hz (heart-rate 180 BPM) ensuring correct measurement over a wide range of heart rate values.

Also, the heart rate estimation module 120 performs Fourier transform (FFT) on the pre-processed signals and obtains power spectrum of the PPG and acceleration signals. The heart rate estimation module 120 then analyzes the power spectra of PPG and acceleration signals to check whether the assumed heart peak is true or it is due to the effect of motion. To do this, the highest FFT peak of the PPG signal is taken and a range around that peak (say, +−t Hz) is checked for the presence of any significant acceleration FFT peak in that range. If present, 2 peak features, such as a ratio of power of a first highest PPG peak to that of the nearby acceleration peak, and the reciprocal of power of a second highest PPG peak are taken and using random forest learning method it is decided whether the acceleration peak affects the first PPG peak or not.

In the process of eliminating motion artefacts from PPG-based heart rate estimation, if motion is present during a particular window, the heart rate estimation module 120 analyzes the PPG spectrum for the highest peak. After obtaining the highest PPG peak, the heart rate estimation module 120 check whether any significant acceleration peak (satisfying cfar condition, i.e., rising 50% above the mean of the neighboring peaks) is aligned (lies in the same frequency range) with the PPG peak or not. If such an acceleration peak is found, then the second highest PPG peak is selected. In many cases, small, yet significant acceleration peaks are present aligned with the first PPG peak, but if the PPG peak is considerably strong, and a very small acceleration peak is present, the true heart peak is the first PPG peak itself, but very often, as the acceleration peak satisfies the cfar condition, the first PPG peak is discarded and the second peak is considered as the true heart peak. Hence, it results in erroneous heart rate measurement. To avoid this error, a machine learning technique (Random Forest) is used for defining a method to select the correct peak out of the two PPG peaks, based on the power values of the two PPG peaks and the aligned acceleration peak. If the first peak power is very high compared to the acceleration peak power, and the second PPG peak is considerably weak, the first peak is chosen as the true peak, otherwise, the second peak is chosen, for heart rate estimation.

Generally, random forests or random decision forests are an ensemble learning method for classification, regression and other tasks, that operate by constructing a multitude of decision trees at training time and outputting the class that is the mode of the classes (classification) or mean prediction (regression) of the individual trees. Random decision forests correct for decision trees' habit of overfitting to their training set. In the given context, random forest learning is used to predict which PPG peak (first highest peak, or second highest) corresponds to heart-rate and is to be chosen for calculation of heart-rate in presence of motion. Inherently, random forest algorithm integrates various decision trees and predicts the class that is the mode of classes predicted by individual trees. For doing this, various peaks of the PPG are assessed and consequently 2 features have been taken and right peak is annotated as a class. The two features are as follows:

1. The ratio of highest PPG peak power to the power of the acceleration peak aligned with highest PPG peak.
2. The reciprocal of the power of second highest PPG peak.

CLASSES (True peak):
Class-1: 1st PPG Peak
Class-2: 2nd PPG Peak

Also, the heart rate estimation module 120 uses the above mentioned features to train the random forest model with 80% of the total data collected. The remaining 20% is used for testing. This model generation is performed offline and the generated model is used in real-time classification of the test data. After the training phase is done, and a model is generated, it is used to classify the test dataset, depending on the feature values, whether the first or second PPG peak is to be selected for heart rate estimation.

If it is found that the heart rate estimation is not affected, then the heart rate estimation module 120 considers the first highest peak of PPG signal for heart rate estimation similar to the process when there is no motion. If it is found that the heart rate estimation is affected, then the heart rate estimation module 120 identifies the second highest peak from PPG FFT spectrum and estimates the heart rate using frequency of the peak. In some embodiments, the second highest PPG peak is checked for presence of any nearby significant acceleration peak, and if any such peak is found, the window is considered ambiguous and is discarded.

Generally, using a PPG signal is a robust non-invasive optical method to measure the volume of blood flowing in vessels at the peripheral site. The PPG sensor essentially consists of light emitting diode (LED) that illuminates the skin and a photo-diode measures the amount of light either transmitted or reflected through the tissues. The variation of light intensity captured by the photo diode is directly associated with cardiac rhythm. Each cardiac cycle appears as a peak in the PPG signal. Thus, PPG signal contains slowly varying AC components along with DC signal. The AC represents the heart rate signal and the periodicity represents the heart rate. Subsequently, the heart rate is estimated by obtaining the main frequency component of the filtered PPG signal. This is done by performing Fourier Transform and obtaining the frequency of the highest peak from the power spectrum. This frequency (say, f max) is then converted to beats per minute by: HR(BPM)=f max*60.

Further in an example implementation, the wearable device 102 transfers the heart rates estimated in all the windows to the server 106 via the gateway device 104. Here, the heart rate values of the windows (say, for 2 minutes of data) are sent to the server 106 for post processing. In an embodiment, the post processing module 122 forms a histogram with fixed bin size giving weight 2 to heart rate values for windows without motion and weight 1 to those values for windows with motion. Hence, the post processing module 122 selects the most occurring bin and considers its median value as a final heart rate. Thus obtaining a better estimation of a user's heart-rate and can be used for further analysis in the server 106.

Figure 2A:
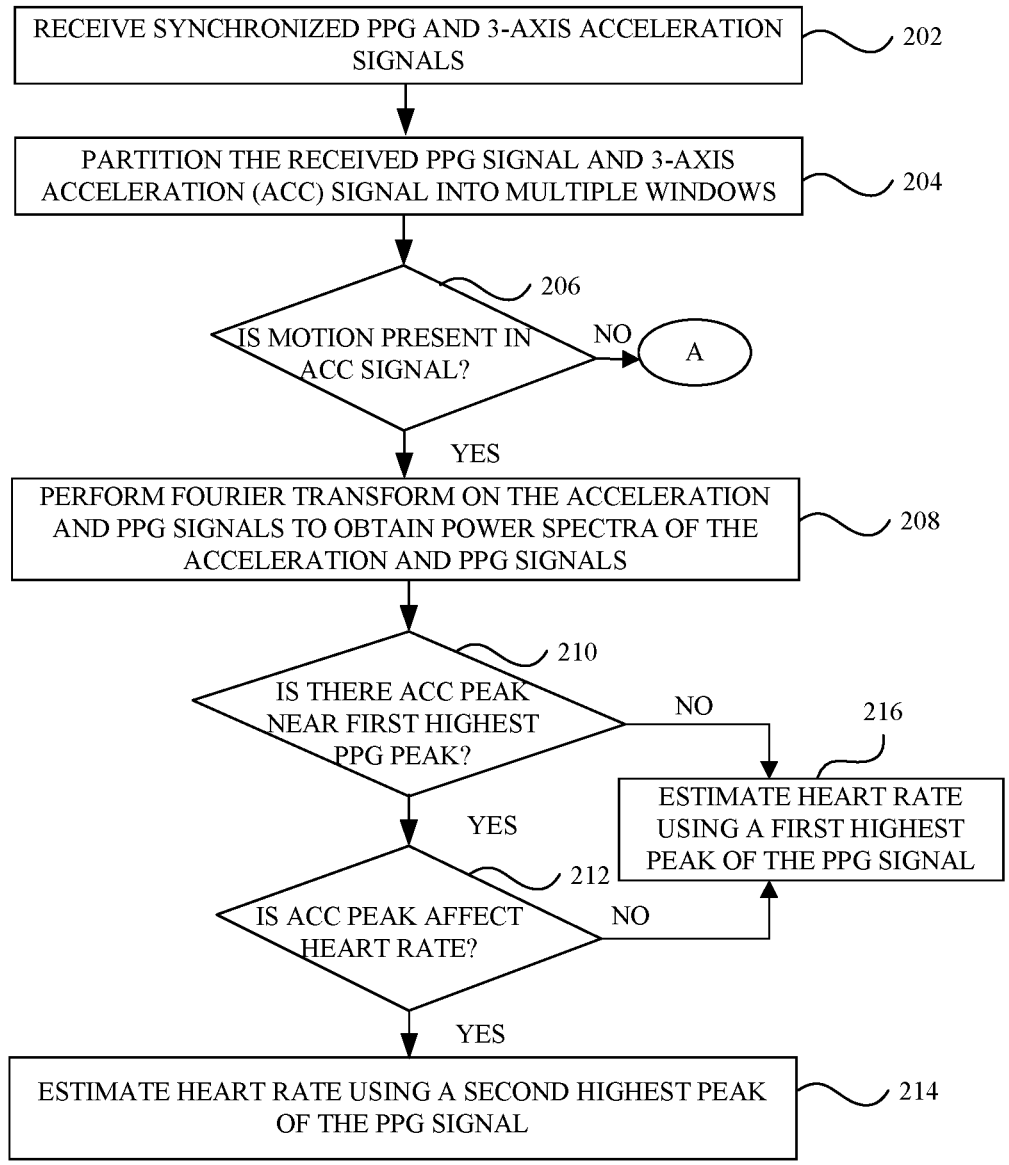

FIGS. 2A and 2B illustrate flow diagrams of methods 200A and 200B for heart rate estimation, in accordance with an example embodiment. The processor-implemented method 200 may be described in the general context of computer executable instructions. Generally, computer executable instructions can include routines, programs, objects, components, data structures, procedures, modules, functions, etc., that perform particular functions or implement particular abstract data types. The method 200 may also be practiced in a distributed computing environment where functions are performed by remote processing devices that are linked through a communication network. The order in which the method 200 is described is not intended to be construed as a limitation, and any number of the described method blocks can be combined in any order to implement the method 200, or an alternative method. Furthermore, the method 200 can be implemented in any suitable hardware, software, firmware, or combination thereof. In an embodiment, the method 200 depicted in the flow chart may be executed by a system, for example, the system 100 of FIG. 1.

At block 202, a synchronized photoplethysmograph (PPG) signal and 3-axis acceleration signal are received from sensors associated with a user of a wearable device. For example, the PPG signal and the 3-axis acceleration signal are obtained at same point of time. At block 204, the received PPG signal and 3-axis acceleration signal are partitioned into multiple windows. In some embodiments, noise from each of the multiple windows of the PPG signal is eliminated based on a threshold value for the PPG signal. Further, direct current (DC) component is removed from each of the multiple windows of the PPG signal upon eliminating the noise.

At block 206, a check is made to determine whether motion is present in one of the multiple windows of the 3-axis acceleration signal based on mean and standard deviation values of the 3-axis acceleration signal in the one of the multiple windows. For example, a check is made to determine whether motion is present in one of the multiple windows of the 3-axis acceleration signal based on a threshold value calculated by the mean and standard deviation of the 3-axis acceleration signal in the one of the multiple windows and a decision tree.

At block 208, Fourier transform is performed on the 3-axis acceleration signal and PPG signal to obtain power spectra of the 3-axis acceleration signal and PPG signal in the one of the multiple windows when there is motion in the one of the multiple windows of the 3-axis acceleration signal, the power spectra includes fast Fourier transform (FFT) peaks of the 3-axis acceleration signal and PPG signal in the one of the multiple windows. At block 210, a check is made to determine whether a peak of the 3-axis acceleration signal is present in a range around a first highest peak of the PPG signal. At block 212, a check is made to determine whether the peak of the 3-axis acceleration signal affects heart rate of the user by performing random forest learning when the peak of the 3-axis acceleration signal is in the range around the first highest peak of the PPG signal. For example, random forest learning is performed based on power values of the first highest peak of the PPG signal, a second highest peak of the PPG signal and the peak of the 3-axis acceleration signal.

At block 214, the heart rate of the user in the one of the multiple windows is estimated using a second highest peak of the PPG signal when the peak of the 3-axis acceleration signal affects heart rate of the user. At block 216, the heart rate of the user in the one of the multiple windows is estimated using the identified first highest peak of the PPG signal when at least one of the peak of the 3-axis acceleration signal is not present in a range around the highest peak of the PPG signal and the peak of the 3-axis acceleration signal does not affect heart rate of the user.

At block 218, zero-phase digital filtering of the PPG signal in the one of the multiple windows is performed when there is no motion in the one of the multiple windows of the 3-axis acceleration signal at block 206. At block 220, Fourier transform is performed on the filtered PPG signal to obtain power spectra of the PPG signal in the one of the multiple windows, the power spectra includes FFT peaks of the PPG signal in the one of the multiple windows. At 222, peak ambiguity check is performed to determine whether the window is noisy. If so, receive other input signals from the wearable device. If not, at block 224, the heart rate of the user in the one of the multiple windows is estimated using a highest FFT peak of the PPG signal. Further, heart rate of the user is estimated in remaining windows by repeating at least one of the above steps.

In some embodiments, a histogram with a predefined bin size is formed for the heart rates of the user in the multiple windows. Further, a bin with a highest number of occurrence in the histogram is selected. Furthermore, a median value of the selected bin is considered as a heart rate of the user.

The various embodiments described in FIGS. 1-3 propose a technique for heart rate estimation based on effects of motion due to crane vibrations and hand movements. The technique estimates heart rate estimates using minimal low-cost light hardware feasible to be implemented in real-time. In this technique, a mobility checking is deployed to determine the degree of motion while the crane operator is wearing the device. According to the decision, different algorithm is implied to estimate the heart rate of the user. While is static mode, the conventional frequency based algorithm is opted whereas in motion, more complex approach is involved in heart rate estimation. This dual approach provides the flexibility and avoids the computational complexity while the device is not in motion. Thus helping in reduction of processing, memory space with a low signal sampling rate (50 Hz) and power consumption in the wearable device. Further, the technique is feasible to be implemented in real-time wearable devices and helps in using low-cost light wearable device especially in environments where it is difficult to install complicated hardware.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is, however to be understood that the scope of the protection is extended to such a program and in addition to a computer-readable means having a message therein; such non-transitory machine readable information storage mediums contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The foregoing description of the specific implementations and embodiments will so fully reveal the general nature of the implementations and embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A processor-implemented method comprising:
   (a) receiving, by one or more hardware processors, synchronized photoplethysmograph (PPG) signal and 3-axis acceleration signal from sensors associated with a user of a wearable device;
   (b) partitioning, by the one or more hardware processors, the received PPG signal and 3-axis acceleration signal into multiple windows;
   (c) determining, by the one or more hardware processors, whether motion is present in one of the multiple windows of the 3-axis acceleration signal based on a decision tree comprising mean and standard deviation values of the 3-axis acceleration signal in one of the multiple windows, wherein the decision tree for determining whether motion is present in one of the multiple windows of the 3-axis acceleration signal is trained with ground truth observations that are annotated as static or motion;
   (d) pre-processing, by the one or more hardware processors, the 3-axis acceleration signal and PPG signal by performing zero-phase digital filtering in the one of the multiple windows when there is motion in the one of the multiple windows of the 3-axis acceleration signal, using a filtfilt filter;
   (e) performing, by the one or more hardware processors, Fourier transform on the pre-processed 3-axis acceleration signal and PPG signal to obtain power spectra of the 3-axis acceleration signal and PPG signal in the one of the multiple windows when there is motion in the one of the multiple windows of the 3-axis acceleration signal, wherein the power spectra comprises fast Fourier transform (FFT) peaks of the 3-axis acceleration signal and PPG signal in the one of the multiple windows;
   (f) determining, by the one or more hardware processors, whether a peak of the 3-axis acceleration signal is present in a range around a first highest peak of the PPG signal;
   (g) determining, by the one or more hardware processors, whether the peak of the 3-axis acceleration signal indicates the motion of the user is interfering with the first highest peak of the PPG signal by performing random forest learning on two peak features when the peak of the 3-axis acceleration signal is in the range around the first highest peak of the PPG signal, wherein the two peak features comprise i) a ratio of power of the first highest peak of the PPG signal to that of the determined 3-axis acceleration signal peak present in the range around the first highest peak of the PPG signal, and ii) reciprocal of power of a second highest peak of the PPG signal, and wherein based on the random forest learning on the two peak features, one among the first highest peak of the PPG signal and the second highest peak of the PPG signal is identified as a true heart peak; and
   (h) estimating, by the one or more hardware processors, the heart rate of the user in the one of the multiple windows using the second highest peak of the PPG signal that is identified as the true heart peak, when the peak of the 3-axis acceleration signal indicates the motion of the user is interfering with the first highest peak of the PPG signal.

2. The method as claimed in claim 1, further comprising:
   (i) estimating, by the one or more hardware processors, the heart rate of the user in the one of the multiple windows using the first highest peak of the PPG signal when at least one of the peak of the 3-axis acceleration signal indicating the motion of the user, is not present in a range around the first highest peak of the PPG signal and the peak of the 3-axis acceleration signal indicating the motion of the user, does not interfere with the heart rate of the user.

3. The method as claimed in claim 1, further comprising:
(j) performing, by the one or more hardware processors, zero-phase digital filtering of the PPG signal in the one of the multiple windows when there is no motion in the one of the multiple windows of the 3-axis acceleration signal;
(k) performing, by the one or more hardware processors, Fourier transform on the filtered PPG signal to obtain power spectra of the PPG signal in the one of the multiple windows, wherein the power spectra comprises FFT peaks of the PPG signal in the one of the multiple windows; and
(l) estimating, by the one or more hardware processors, the heart rate of the user in the one of the multiple windows using a highest peak of the PPG signal.

4. The method as claimed in claim 3, further comprising:
estimating, by the one or more hardware processors, the heart rate of the user in remaining windows by repeating at least one of the steps of (c)-(h) and (j)-(l).

5. The method as claimed in 4, further comprising:
forming, by the one or more hardware processors, a histogram with a predefined bin size for the heart rates of the user in the multiple windows;
selecting, by the one or more hardware processors, a bin with a highest number of occurrence in the histogram; and
considering, by the one or more hardware processors, a median value of the selected bin as a heart rate of the user.

6. The method as claimed in claim 1, further comprising:
eliminating, by the one or more hardware processors, noise from each of the multiple windows of the PPG signal based on a threshold value for the PPG signal; and
removing, by the one or more hardware processors, direct current (DC) component from each of the multiple windows of the PPG signal upon eliminating the noise.

7. A system comprising:
a wearable device (102) associated with a user, wherein the wearable device comprises:
multiple sensors (112);
one or more memories (110); and
one or more hardware processors (108), the one or more memories coupled to the one or more hardware processors, wherein the one or more hardware processors are configured to execute programmed instructions stored in the one or more memories to:
(a) receive synchronized photoplethysmograph (PPG) signal and 3-axis acceleration signal from the multiple sensors;
(b) partition the received PPG signal and 3-axis acceleration signal into multiple windows;
(c) determine whether motion is present in one of the multiple windows of the 3-axis acceleration signal based on a decision tree comprising mean and standard deviation values of the 3-axis acceleration signal in one of the multiple windows, wherein the decision tree for determining whether motion is present in one of the multiple windows of the 3-axis acceleration signal is trained with ground truth observations that are annotated as static or motion;
(d) pre-process the 3-axis acceleration signal and PPG signal by performing zero-phase digital filtering in the one of the multiple windows when there is motion in the one of the multiple windows of the 3-axis acceleration signal, using a filtfilt filter;
(e) perform Fourier transform on the pre-processed 3-axis acceleration signal and PPG signal to obtain power spectra of the 3-axis acceleration signal and PPG signal in the one of the multiple windows when there is motion in the one of the multiple windows of the 3-axis acceleration signal, wherein the power spectra comprises fast Fourier transform (FFT) peaks of the 3-axis acceleration signal and PPG signal in the one of the multiple windows;
(f) determine whether a peak of the 3-axis acceleration signal is present in a range around a first highest peak of the PPG signal;
(g) determine whether the peak of the 3-axis acceleration signal indicates the motion of the user is interfering with the first highest peak of the PPG signal by performing random forest learning on two peak features when the peak of the 3-axis acceleration signal is in the range around the first highest peak of the PPG signal, wherein the two peak features comprise i) a ratio of power of the first highest peak of the PPG signal to that of the determined 3-axis acceleration signal peak present in the range around the first highest peak of the PPG signal, and ii) reciprocal of power of a second highest peak of the PPG signal, and wherein based on the random forest learning on the two peak features, one among the first highest peak of the PPG signal and the second highest peak of the PPG signal is identified as a true heart peak; and
(h) estimate the heart rate of the user in the one of the multiple windows using the second highest peak of the PPG signal that is identified as the true heart peak, when the peak of the 3-axis acceleration signal indicates the motion of the use r is interfering with the first highest peak of the PPG signal.

8. The system as claimed in claim 7, wherein the one or more hardware processors are further configured to execute programmed instructions to:
(i) estimate the heart rate of the user in the one of the multiple windows using the first highest peak of the PPG signal when at least one of the peak of the 3-axis acceleration signal indicating the motion of the user, is not present in a range around the first highest peak of the PPG signal and the peak of the 3-axis acceleration signal indicating the motion of the user, does not interfere with the heart rate of the user.

9. The system as claimed in claim 7, wherein the one or more hardware processors are further configured to execute programmed instructions to:
(j) perform zero-phase digital filtering of the PPG signal in the one of the multiple windows when there is no motion in the one of the multiple windows of the 3-axis acceleration signal;
(k) perform Fourier transform on the filtered PPG signal to obtain power spectra of the PPG signal in the one of the multiple windows, wherein the power spectra comprises FFT peaks of the PPG signal in the one of the multiple windows; and
(l) estimate the heart rate of the user in the one of the multiple windows using a highest FFT peak of the PPG signal.

10. The system as claimed in claim 9, wherein the one or more hardware processors are further configured to execute programmed instructions to:
   estimate a heart rate of the user in remaining windows by repeating at least one the steps of (c)-(h) and (j)-(l).

11. The system as claimed in claim 10, further comprising:
   a server (106) communicatively coupled to the wearable device (102), wherein the server comprises:
   one or more memories (118); and
   one or more hardware processors (116) communicatively coupled to the one or more memories (118), wherein the one or more hardware processors are configured to execute programmed instructions in the one or more memories to:
      form a histogram with a predefined bin size for the heart rates of the user in the multiple windows;
      select a bin with a highest number of occurrence in the histogram; and
      consider a median value of the selected bin as a heart rate of the user.

12. The system as claimed in claim 7, wherein the one or more hardware processors are further configured to execute programmed instructions to:
   eliminate noise from each of the multiple windows of the PPG signal based on a threshold value for the PPG signal; and
   remove direct current (DC) component from each of the multiple windows of the PPG signal upon eliminating the noise.

13. One or more non-transitory machine readable information storage mediums comprising one or more instructions which when executed by one or more hardware processors causes:
   (a) receiving, by the one or more hardware processors, synchronized photoplethysmograph (PPG) signal and 3-axis acceleration signal from sensors associated with a user of a wearable device;
   (b) partitioning, by the one or more hardware processors, the received PPG signal and 3-axis acceleration signal into multiple windows;
   (c) determining, by the one or more hardware processors, whether motion is present in one of the multiple windows of the 3-axis acceleration signal based on a decision tree comprising mean and standard deviation values of the 3-axis acceleration signal in the one of the multiple windows, wherein the decision tree for determining whether motion is present in one of the multiple windows of the 3-axis acceleration signal is trained with ground truth observations that are annotated as static or motion;
   (d) pre-processing, by the one or more hardware processors, the 3-axis acceleration signal and PPG signal by performing zero-phase digital filtering in the one of the multiple windows when there is motion in the one of the multiple windows of the 3-axis acceleration signal, using a filtfilt filter;
   (e) performing, by the one or more hardware processors, Fourier transform on the filtered 3-axis acceleration signal and PPG signal to obtain power spectra of the 3-axis acceleration signal and PPG signal in the one of the multiple windows when there is motion in the one of the multiple windows of the 3-axis acceleration signal, wherein the power spectra comprises fast Fourier transform (FFT) peaks of the 3-axis acceleration signal and PPG signal in the one of the multiple windows;
   (f) determining, by the one or more hardware processors, whether a peak of the 3-axis acceleration signal is present in a range around a first highest peak of the PPG signal;
   (g) determining, by the one or more hardware processors, whether the peak of the 3-axis acceleration signal indicates the motion of the user is interfering with the first highest peak of the PPG signal by performing random forest learning on two peak features when the peak of the 3-axis acceleration Signal is in the range around the first highest peak of the PPG signal, wherein the two peak features comprise i) a ratio of power of the first highest peak of the PPG signal to that of the determined 3-axis acceleration signal peak present in the range around the first highest peak of the PPG signal, and ii) reciprocal of power of a second highest peak of the PPG signal, and wherein based on the random forest learning on the two peak features, one among the first highest peak of the PPG signal and the second highest peak of the PPG signal is identified as a true heart peak; and
   (h) estimating, by the one or more hardware processors, the heart rate of the user in the one of the multiple windows using the second highest peak of the PPG signal that is identified as the true heart peak, when the peak of the 3-axis acceleration signal indicates the motion of the user is interfering with the first highest peak of the PPG signal.

* * * * *